United States Patent
Sjödin et al.

(10) Patent No.: US 8,063,371 B2
(45) Date of Patent: Nov. 22, 2011

(54) DEVICE FOR INDICATING ILLICIT SUBSTANCES IN THE EXHALATION AIR OF A MACHINE OPERATOR

(76) Inventors: Kurt Sjödin, Hässelby (SE); Adam Hedman, Uppsala (SE)

(*) Notice: Subject to any disclaimer, the term of this patent is extended or adjusted under 35 U.S.C. 154(b) by 335 days.

(21) Appl. No.: 12/299,707

(22) PCT Filed: May 7, 2007

(86) PCT No.: PCT/SE2007/000436
§ 371 (c)(1),
(2), (4) Date: Nov. 5, 2008

(87) PCT Pub. No.: WO2007/133142
PCT Pub. Date: Nov. 22, 2007

(65) Prior Publication Data
US 2009/0236527 A1    Sep. 24, 2009

(30) Foreign Application Priority Data
May 11, 2006  (SE) ..................... 0601054

(51) Int. Cl.
*G01N 21/00* (2006.01)
*G01J 5/02* (2006.01)
(52) U.S. Cl. ............................ 250/338.5; 250/339.13
(58) Field of Classification Search ............... 250/338.5, 250/340, 343, 282, 492.1, 492.3, 339.08, 250/339.13, 288; 600/504
See application file for complete search history.

(56) References Cited

U.S. PATENT DOCUMENTS

| | | | | |
|---|---|---|---|---|
| 3,792,272 A * | 2/1974 | Harte et al. | ................... | 250/343 |
| 4,268,751 A | 5/1981 | Fritzlen et al. | | |
| 5,349,187 A | 9/1994 | Azzazy et al. | | |
| 7,173,536 B2 * | 2/2007 | Duval | .......................... | 340/576 |

FOREIGN PATENT DOCUMENTS

| | | |
|---|---|---|
| EP | 1441212 A1 | 7/2004 |
| EP | 1688741 A2 | 8/2006 |
| GB | 2150725 A | 7/1985 |
| WO | 0212883 A1 | 2/2002 |

OTHER PUBLICATIONS

PCT International Search Report, mailed Aug. 17, 2007, in connection with International Application No. PCT/SE2007/000436.
PCT International Preliminary Report on Patentability, mailed Nov. 11, 2008, in connection with International Application No. PCT/SE2007/000436.

* cited by examiner

*Primary Examiner* — David Porta
*Assistant Examiner* — Faye Boosalis
(74) *Attorney, Agent, or Firm* — Potomac Patent Group PLLC

(57) ABSTRACT

A device for a continuous indication of illicit substances in the exhalation air of face of the machine operator comprises an IR source and an IR detector being sensitive to wave length having an absorbance of the illicit substance, whereby the beam path of the IR source to the detector runs in front of the face of the operator.

3 Claims, 1 Drawing Sheet

Figure 1:
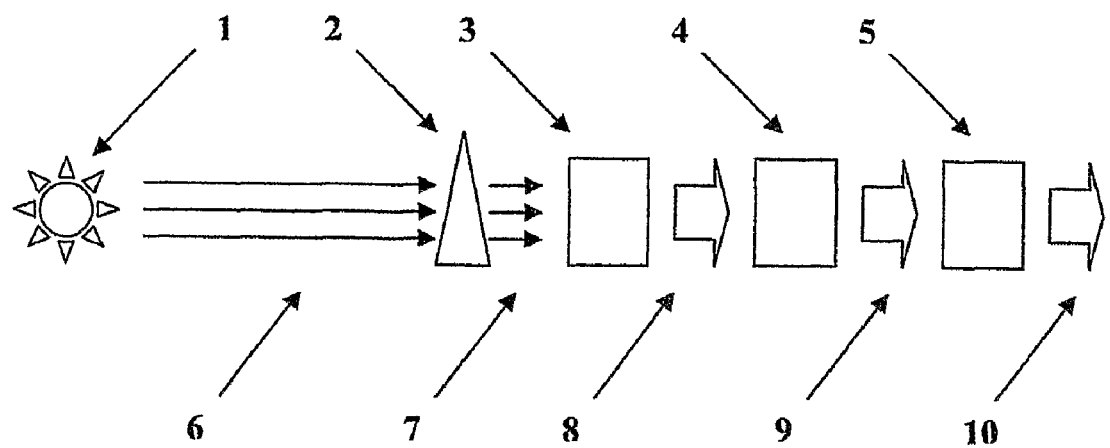

DEVICE FOR INDICATING ILLICIT SUBSTANCES IN THE EXHALATION AIR OF A MACHINE OPERATOR

FIELD OF THE INVENTION

The present invention refers to an advice for indicating illicit substances such as ethanol in the exhalation air of a machine operator e.g. a driver of a vehicle.

BACKGROUND OF THE INVENTION

Operators/drivers of vehicles, boats, aircraft, trains, traverses and other machines are in a position demanding tense watchfulness and high reaction ability so as not to cause accidents. The influence of different substances, such as alcohol may seriously deteriorate judgment, time of reaction and also other abilities giving rise to an increased risk for accidents.

So called alcohol interlocks were initially used in Canada and the US and are now also in use e. g. in Sweden. Initially the systems were only used in vehicles used by persons convicted in court to install them in order to keep their drivers' licenses. The monitoring system implied that they should, within short intervals, visit a service firm which scrutinized the information stored in the system concerning the defects and violations.

In Sweden this type of alcohol interlocks has also achieved great use for voluntary mounting in primarily commercial vehicles. The operation normally implies that the vehicle cannot be started if the concentration of alcohol of the exhalation air exceeds a predetermined value.

The interest in monitoring the soberness of drivers in various types of vehicles has considerably increased lately. Several manufacturers market alcohol interlocks for vehicles. All these products are based on active systems which require the driver to make a heavy blow through a mouth piece. Detection is made by means of a fuel cell or a semiconductor.

Although there has been a development aiming at preventing the manipulation of the alcohol test result, several essential drawbacks remain in existing systems. Thus none of the presently used systems has any function for checking if the driver is the person providing the sample. A certain check-up of his identity may however be performed by demanding from the driver after some driving a further exhalation air sample. The simplest systems do not even imply a feature checking that it is a human being who provides the exhalation air sample. Systems approved by the authorities do however demand, e.g. that the blowing person simultaneously must perform a "hum tone", the purpose thereof being to prevent that a sample delivered by an air pump or a balloon may be approved. Furthermore the exhalation air sample should derive from the deep lung air in order to give a fully correct result. That this is the fact is usually checked by requiring a certain minimum volume passing through the instrument before approval of the sample, which implies that persons with a decreased lung capacity may experience a difficulty in giving an approved sample. Thus, a driver may in chilly weather by taking a few deep breaths chill the mouth cavity and thereupon deliver a sample giving rise to a lower measuring result.

It can furthermore be noted that existing systems are not particularly user-friendly. It may e.g. at a low temperature require several minutes before the instrument by means of heating reaches a temperature enabling sampling. Also the detector of the instrument has to be initially heated to reach the temperature needed to give correct results and condensation in hoses and tubes may disturb the measuring and have to be avoided. Furthermore existing systems comprise a measuring unit formed by a separate hand-hold device which is difficult to locate in present-day vehicles without the unit itself or its connection to the electrical system of the vehicle being in the way. The cable connecting the measuring unit is usually the part of the system which is most frequently damaged. Furthermore many drivers experience the personal integrity to be affected. There exists a general disinclination for using an equipment requiring a fully visible blowing through a measuring instrument before a vehicle may be used.

Thus there is a need for a device for a non-active system, not requiring the blowing through a mouth-piece by the driver.

In the European Patent Application 1 688 741 there is described a chemical vapor sensor which, in addition to the conventional active (mouthpiece) measuring mode which in a conventional way is used for enabling the starting up of the vehicle, also provides for a passive measurement mode also using a measuring chamber used e.g. for detecting the ethanol vapor in a vehicle cabin. However, since this measurement is made without any reference value it requires an absorber and a heater in order to make an accumulated measurement over an extended period of time and it is even so only an estimate of the alcohol concentration in the cabin not necessarily related to the exhalation air of the driver is made.

It is therefore an object of the present invention to provide a device which eliminates the disadvantages of the active systems described above, i.e. essentially makes it impossible to manipulate and is furthermore extremely user-friendly. The characteristics of the invention will appear from the claims following the specification.

DESCRIPTION OF THE INVENTION

The invention will now be described in detail by means of an example and referring to the enclosed drawing in which:

FIG. 1 schematically shows a device according to the invention and

Figure 2:
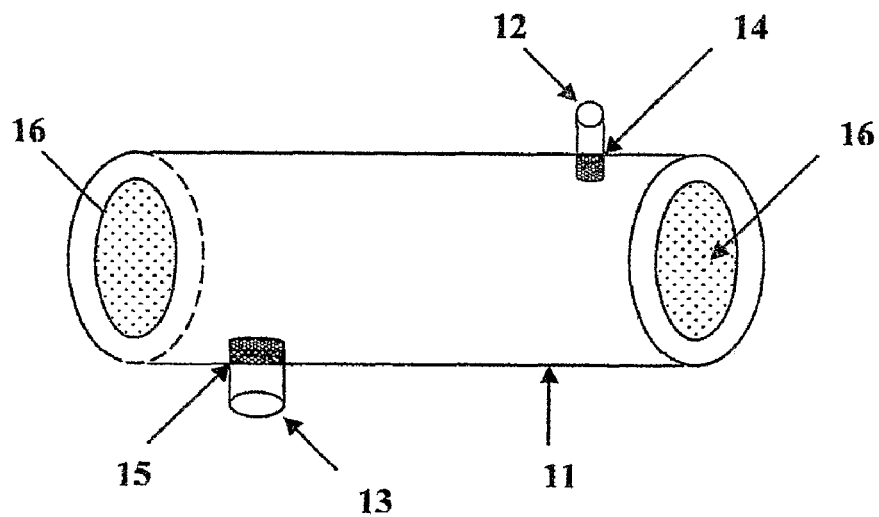

FIG. 2 schematically shows a sampling chamber to be used in the device according to the invention for carrying out an active exhalation sample or for calibration/verification or analysis of another gas sample.

In FIG. 1 reference 1 denotes an IR source transmitting a light beam 6 through the air to be analyzed. The beam path 6 is arranged closed to the face of an operator (not shown), e.g. a vehicle driver, and reaches one or several optical analysers 2 located in front of an IR detector 3 measuring the intensity of the IR light. According to the example the optical filters 2 are adapted to wavelengths having a high absorption for ethanol and a reference wavelength not being affected by ethanol and the IR source and the optical filters are stationary mounted in front of the driver in the cabin of a vehicle, i.e. where possibly exhalated alcohol has its highest concentration. The signal is transmitted from a detector 3 for electronic signal processing to a processor 4 for a digital signal conversion and further to an interface 5 into the machine which the signal generated possibly shall affect. Reference 7 denotes the filtered and deflected IR light having specific wavelengths, reference 8 a filtered and adjusted analogue signal and reference 9 denotes computerized digital information. Reference 10 denotes a machine specific signal which in some way or other affects the machine handled by the operator. The effect might e.g. be that the vehicle will not be able to start if the concentration of ethanol in the IR light 6 exceeds a certain level.

In the device schematically shown in FIG. 1 where the infra-red beam passes through the air in front of the driver there is a full certainty that the sample is delivered by the operator. The inhalation and exhalation air of the driver is continuously analyzed and compared and e.g. an increase of ethanol in the exhalation air over the inhalation air will be immediately detected and can be measured with acceptable accuracy. Furthermore any attempt of manipulating the sample will be detected immediately by the instrument as the signal of the detector will deviate from the curve shape normally delivered and furthermore there will be carried out a measuring of normal breathing and not only the deep lung air. Also an abnormal breathing aiming at chilling the respiratory passages will be detected after a few breaths.

The device according to FIG. 1 will furthermore be extremely user-friendly since the sample is made at normal breathing and it is easy for anyone to give samples which can be analyzed. Furthermore the measurement is made in open air by using IR technique which means that the measuring can be started immediately when the operator takes the seat monitored. The system for measuring in open air has no movable parts. All parts are solidly mounted and integrated which protects the personal integrity as the operator can act as usual and no-one will note that his soberness is checked.

If convenient the device according to FIG. 1 may be modified in that the light-source 1 is located in some more suitable place and the IR light is transmitted to a suitable position via a system of one or several mirrors or light conductors.

The processor 4 suitably comprises software treating the measuring signals and compares the result with parameters stored. A result indicating presence of alcohol will be transmitted to the electronics of the driver and will activate a warning system and/or functions which prevent a driver affected by alcohol from using the vehicle. If the exhalation air contains alcohol the system may thereby demand the performance of an active exhalation sample before further driving of the vehicle is possible.

FIG. 2 schematically shows a sampling chamber which can be used for the performance of such an active exhalation air sample and thereby using the light source and detection equipment of the device according to the invention. This sampling chamber can also be used for the calibration and verification of the analysis system and for the analysis of other gases. In FIG. 2 reference 11 denotes a measuring chamber suitably introduced in the device according to FIG. 1 and where the gas to be analysed will be introduced via a tube 12 provided with a non-return valve 14. The air will then pass through and out from the chamber via an exit tube 13 likewise provided with a non-return valve 15. The spring loaded non-return valves make the final air stay in the chamber until the analysis is terminated. The chamber is further provided with lenses 16 to enable the IR beam according to FIG. 1 to penetrate the sample chambers towards the detector. In case of a reflected beam the chamber may alternatively be provided with a lens at one end and a reflector at the other end.

In the analysis the measuring chamber is located so as to make the IR beam penetrate into the chamber and either being reflected against the IR detector or being directed directly towards the detector. The concentration of ethanol in the expiration air in the measuring chamber will then be measured at high precision. The IR measuring should be made continuously during the blowing moment. This will only be possible if the chamber is located within the IR beam, i.e. it is located in front of the face of the driver aligned to the beam. The correct location can be ensured by having a tone signal indicating this location.

Thus the present invention provides for a system which completely eliminates the disadvantages of the active systems presently existing by providing a passive system having an accuracy and a sensitivity which it has hitherto not been able to achieve. The device according to the invention can not be manipulated and is extremely user friendly and furthermore protects the personal integrity as the operator can behave in a normal way without the environment being able to detect that the soberness is being checked.

We claim:

1. A device for indicating an illicit substance in exhalation air of a machine operator, comprising:
   an infrared (IR) light source and an IR light detector located to make inhalation air and exhalation air of the operator pass in open air between the IR light source and the IR light detector, wherein the detector is provided with a filter having at least one wave length of high IR absorbance for the illicit substance; and
   means, coupled to the detector, for analyzing differences in concentration of the illicit substance in the inhalation air and exhalation air.

2. The device of claim 1, wherein the illicit substance is ethanol.

3. The device of claim 1, wherein the machine operator is a driver of a vehicle.

* * * * *